(12) United States Patent
Palreddy et al.

(10) Patent No.: US 6,917,830 B2
(45) Date of Patent: Jul. 12, 2005

(54) METHOD AND SYSTEM FOR NOISE MEASUREMENT IN AN IMPLANTABLE CARDIAC DEVICE

(75) Inventors: Surekha Palreddy, Vadnais Heights, MN (US); Carlos Ricci, Apple Valley, MN (US); Yayun Lin, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 10/643,770

(22) Filed: Aug. 19, 2003

(65) Prior Publication Data

US 2004/0106957 A1 Jun. 3, 2004

Related U.S. Application Data

(63) Continuation-in-part of application No. 10/046,650, filed on Oct. 29, 2001, and a continuation-in-part of application No. 10/213,364, filed on Aug. 6, 2002.

(51) Int. Cl.$^7$ ............................................. A61B 5/04
(52) U.S. Cl. .......................... 600/509; 607/607; 607/9; 128/901
(58) Field of Search ....................... 600/509, 521, 600/506; 607/2, 27, 62, 9; 128/901, 902

(56) References Cited

U.S. PATENT DOCUMENTS

| 4,432,362 A | | 2/1984 | Leckrone et al. ............... 607/9 |
|---|---|---|---|
| 4,589,420 A | * | 5/1986 | Adams et al. ............... 600/515 |
| 4,679,144 A | * | 7/1987 | Cox et al. .................... 600/516 |
| 4,779,617 A | | 10/1988 | Whigham ............... 128/419 P |
| 4,913,146 A | | 4/1990 | DeCote, Jr. .................. 128/419 |
| 4,960,123 A | * | 10/1990 | Maker ............................ 607/4 |
| 5,010,887 A | | 4/1991 | Thornander ................. 128/696 |
| 5,188,117 A | | 2/1993 | Steinhaus et al. ........... 128/708 |
| 5,209,237 A | | 5/1993 | Rosenthal ................... 128/698 |
| 5,492,128 A | | 2/1996 | Wickham .................... 128/696 |
| 5,522,857 A | | 6/1996 | van Krieken .................. 607/9 |
| 5,562,713 A | | 10/1996 | Silvian ......................... 607/32 |
| 5,564,430 A | | 10/1996 | Jacobson et al. ........... 128/697 |
| 5,573,550 A | | 11/1996 | Zadeh et al. .................. 607/28 |
| 5,591,214 A | | 1/1997 | Lu ................................ 607/9 |
| 5,613,495 A | | 3/1997 | Mills et al. ................. 128/696 |
| 5,647,379 A | | 7/1997 | Meltzer ...................... 128/891 |
| 5,697,958 A | | 12/1997 | Paul et al. .................... 607/31 |
| 5,702,425 A | | 12/1997 | Wickham ....................... 607/9 |

(Continued)

FOREIGN PATENT DOCUMENTS

WO     WO-01/43820     6/2001     ............ A61N/1/37

OTHER PUBLICATIONS

Gunderson, Bruce, "Automatic Identification of ICD Lead Problems Using Electrograms", *PACE*, vol. 24, p. 664, Apr. 2002, (2002), 664.

"International Search Report from corresponding PCT Application No. PCT/US2004/026993", (Nov. 18, 2004), 3 pages.

*Primary Examiner*—Kennedy Schaetzle
(74) *Attorney, Agent, or Firm*—Schwegman, Lundberg, Woessner & Kluth, P.A.

(57) ABSTRACT

An implantable cardiac rhythm management device is configured to estimating the noise level and noise floor in a sensing channel by measuring the magnitude of signal in the sensing channel when noise is determined to be present or absent, respectively. The presence or absence of noise may be determined by computing the density of local peaks or inflection points in an electrogram waveform. The computed local peak density is then used to set or clear a noise flag, which signifies whether noise is present or not. A noise statistic computed from samples of the electrogram signal obtained through a sensing channel may then be used to estimate a noise level or a noise floor.

25 Claims, 2 Drawing Sheets

OTHER PUBLICATIONS

| | | | | |
|---|---|---|---|---|
| 5,702,427 | A | | 12/1997 | Ecker et al. ............... 607/28 |
| 5,709,215 | A | | 1/1998 | Perttu et al. ............. 128/708 |
| 5,755,738 | A | | 5/1998 | Kim et al. .................. 607/9 |
| 5,766,227 | A | * | 6/1998 | Nappholz et al. ............ 607/9 |
| 5,778,881 | A | | 7/1998 | Sun et al. ................ 128/696 |
| 5,782,876 | A | | 7/1998 | Flammang ................. 607/4 |
| 5,792,212 | A | | 8/1998 | Weijand ................... 607/73 |
| 5,817,130 | A | | 10/1998 | Cox et al. ................. 607/5 |
| 5,817,135 | A | | 10/1998 | Cooper et al. ............. 607/17 |
| 5,861,008 | A | * | 1/1999 | Obel et al. ................ 607/11 |
| 5,865,749 | A | | 2/1999 | Doten et al. ............. 600/443 |
| 5,867,361 | A | | 2/1999 | Wolf et al. .............. 361/302 |
| 5,870,272 | A | | 2/1999 | Seifried et al. ........... 361/302 |
| 5,871,509 | A | | 2/1999 | Noren ..................... 607/9 |
| 5,891,171 | A | | 4/1999 | Wickham ................. 607/4 |
| 5,897,575 | A | | 4/1999 | Wickham ................. 607/4 |
| 5,957,857 | A | * | 9/1999 | Hartley .................. 600/521 |
| 5,978,710 | A | | 11/1999 | Prutchi et al. ............ 607/17 |
| 5,999,848 | A | | 12/1999 | Gord et al. ............... 607/2 |
| 6,029,086 | A | * | 2/2000 | Kim et al. ................. 607/9 |
| 6,031,710 | A | | 2/2000 | Wolf et al. .............. 361/302 |
| 6,063,034 | A | | 5/2000 | Doten et al. ............. 600/448 |
| 6,068,589 | A | | 5/2000 | Neukermans .............. 600/25 |
| 6,070,097 | A | | 5/2000 | Kreger et al. ............ 600/521 |
| 6,112,119 | A | * | 8/2000 | Schuelke et al. ............ 607/9 |
| 6,195,585 | B1 | | 2/2001 | Karunasiri et al. ......... 607/57 |
| 6,198,968 | B1 | | 3/2001 | Prutchi et al. ............. 607/9 |
| 6,201,993 | B1 | | 3/2001 | Kruse et al. .............. 607/30 |
| 6,208,900 | B1 | | 3/2001 | Ecker et al. .............. 607/17 |
| 6,223,083 | B1 | | 4/2001 | Rosar ..................... 607/60 |
| 6,230,059 | B1 | | 5/2001 | Duffin .................... 607/60 |
| 6,236,882 | B1 | | 5/2001 | Lee et al. ............... 600/509 |
| 6,272,381 | B1 | | 8/2001 | Callaghan et al. .......... 607/26 |
| 6,282,446 | B1 | | 8/2001 | Eberle et al. .............. 607/5 |
| 6,321,115 | B1 | * | 11/2001 | Mouchawar et al. .......... 607/9 |
| 6,421,554 | B1 | * | 7/2002 | Lee et al. ............... 600/509 |
| 6,505,071 | B1 | | 1/2003 | Zhu et al. |
| 2003/0083713 | A1 | | 5/2003 | Palreddy et al. ........... 607/28 |
| 2004/0030256 | A1 | | 2/2004 | Lin ...................... 600/509 |
| 2004/0106957 | A1 | | 6/2004 | Palreddy et al. ............ 607/9 |

* cited by examiner

# METHOD AND SYSTEM FOR NOISE MEASUREMENT IN AN IMPLANTABLE CARDIAC DEVICE

CROSS-REFERENCE TO RELATED APPLICATION(S)

This application is a continuation-in-part of U.S. patent application Ser. Nos. 10/046,650 filed Oct. 29, 2001 and Ser. No. 10/213,364, filed Aug. 6, 2002 the specifications of which are incorporated herein by reference.

FIELD OF THE INVENTION

This invention pertains to cardiac rhythm management devices such as pacemakers and implantable cardioverter/defibrillators.

BACKGROUND

Cardiac rhythm management devices are implantable devices that provide electrical stimulation to selected chambers of the heart in order to treat disorders of cardiac rhythm. A pacemaker, for example, is a cardiac rhythm management device that paces the heart with timed pacing pulses. The most common condition for which pacemakers are used is in the treatment of bradycardia, where the ventricular rate is too slow. Atrio-ventricular conduction defects (i.e., AV block) that are permanent or intermittent and sick sinus syndrome represent the most common causes of bradycardia for which permanent pacing may be indicated. If functioning properly, the pacemaker makes up for the heart's inability to pace itself at an appropriate rhythm in order to meet metabolic demand by enforcing a minimum heart rate and/or artificially restoring AV conduction. Other cardiac rhythm management devices are designed to detect atrial and/or ventricular tachyarrhythmias and deliver electrical stimulation in order to terminate the tachyarrhythmia in the form of a cardioversion/defibrillation shock or anti-tachycardia pacing. Certain combination devices may incorporate all of the above functionalities.

Cardiac rhythm management devices such as described above monitor the electrical activity of heart via one or more sensing channels so that pacing pulses or defibrillation shocks can be delivered appropriately. Such sensing channels include implanted leads which have electrodes disposed internally near the heart, which leads may also be used for delivering pacing pulses or defibrillation shocks. Implanted leads, however, may inadvertently have potentials imposed upon them arising from non-cardiac muscle tissue, such as skeletal muscle. This undesirable signal is referred to as myopotential noise. The implanted leads may also act as antennas for extraneous electromagnetic fields, referred to as electromagnetic interference (EMI). Examples of EMI sources include environmental noise, such as 60 Hz power line noise, or radiation from cellular telephones or electronic article surveillance systems. When any of these sources are coupled, either individually or in combination, to the implanted leads of a cardiac rhythm management device, signals are produced in the device's sensing channels which may be misinterpreted as cardiac electrical activity, thus causing inappropriate inhibition of pacing and/or inappropriate delivery of defibrillation shocks. The present invention relates to means for dealing with such noise in cardiac rhythm management devices.

SUMMARY

The present invention relates to a method or system implementable in an implantable cardiac rhythm management device for determining the presence or absence of noise in a sensing channel and estimating the magnitude of that noise, referred to as the noise level. A noise floor may also be estimated by measuring the magnitude of signal in the sensing channel when no noise is determined to be present, during time intervals in between cardiac depolarizations when the cardiac signal is substantially quiescent. In accordance with the invention, the presence or absence of noise is determined by computing the density of local peaks or inflection points in an electrogram waveform. The computed local peak density is then used to set or clear a noise flag, which signifies whether noise is present or not. A noise statistic computed from samples of the electrogram signal obtained through a sensing channel may then be used to estimate a noise level or a noise floor, depending upon whether the noise flag is set or cleared, respectively.

DETAILED DESCRIPTION

As noted above, the presence of noise in the sensing channels of a cardiac rhythm management device may adversely affect its operation if such noise is interpreted as cardiac electrical activity. The present invention relates to a method implementable in an implantable device for detecting when such noise is present and when it is not. During periods when noise is found to be present in a sensing channel, the device may estimate the noise level by computing a noise statistic from the electrogram samples generated by the channel. Such a noise level estimate may then be used to adjust the sensitivity of the sensing channel accordingly. Conversely, during periods when noise is found to be absent, a noise statistic may be computed from the electrogram samples during time intervals in between cardiac depolarizations when the cardiac signal is substantially quiescent to form an estimate of the noise floor. The noise floor estimate may then be similarly used to adjust the sensitivity of the sensing channel when no noise is deemed to present. In an exemplary embodiment, the method is implemented by appropriate programming of the controller of an implantable cardiac rhythm management device as described below.

1. Exemplary Implantable Device Description

Cardiac rhythm management devices are implantable devices that provide electrical stimulation to selected chambers of the heart in order to treat disorders of cardiac rhythm. Such devices are usually implanted subcutaneously on the patient's chest and connected to electrodes by leads threaded through the vessels of the upper venous system into the heart. An electrode can be incorporated into a sensing channel that generates an electrogram signal representing cardiac electrical activity at the electrode site and/or incorporated into a pacing or shocking channel for delivering pacing or shock pulses to the site.

Figure 1:
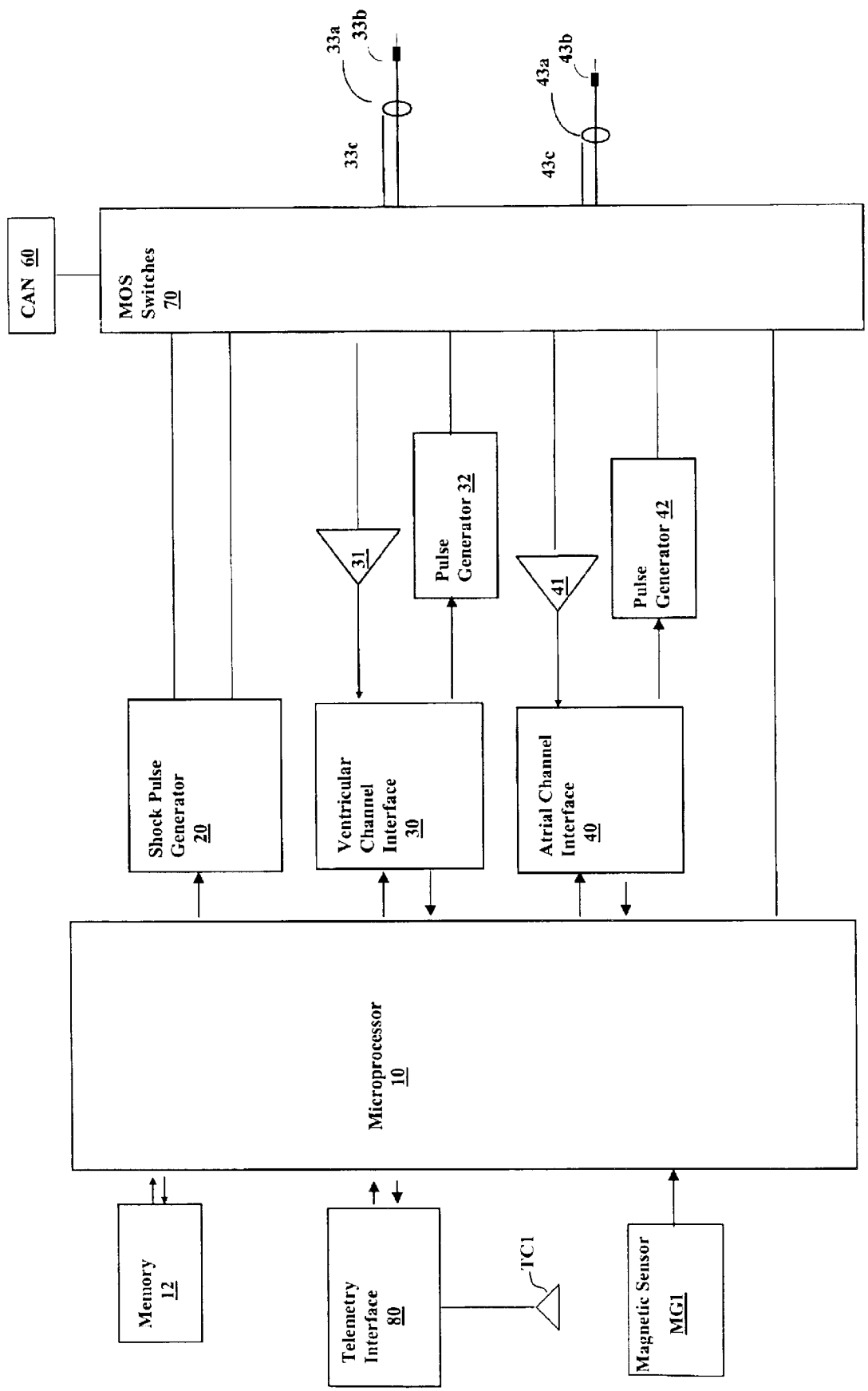
FIG. 1 is a block diagram of an exemplary cardiac rhythm management device for practicing the present invention.

A block diagram of an implantable cardiac rhythm management device is shown in FIG. 1. The controller of the device is made up of a microprocessor 10 communicating with a memory 12 via a bidirectional data bus, where the memory 12 typically comprises a ROM (read-only memory) for program storage and a RAM (random-access memory) for data storage. The controller could be implemented by other types of logic circuitry (e.g., discrete components or programmable logic arrays) using a state machine type of design, but a microprocessor-based system is preferable. As used herein, the programming of a controller should be taken to refer to either discrete logic circuitry configured to perform particular functions or to executable code stored in memory or other storage medium. The controller is capable of operating the device so as to deliver a number of different therapies in response to detected cardiac activity. A telemetry interface 80 is also provided for enabling the controller to communicate with an external programmer.

The embodiment shown in FIG. 1 has two sensing/pacing channels, where a pacing channel is made up of a pulse generator connected to an electrode while a sensing channel is made up of the sense amplifier connected to an electrode. A MOS switch matrix 70 controlled by the microprocessor is used to switch the electrodes from the input of a sense amplifier to the output of a pulse generator. The switch matrix 70 also allows the sensing and pacing channels to be configured by the controller with different combinations of the available electrodes. The channels may be configured as either atrial or ventricular channels. In an example configuration, an atrial sensing/pacing channel includes ring electrode 43a and tip electrode 43b of bipolar lead 43c, sense amplifier 41, pulse generator 42, and a channel interface 40. A ventricular sensing/pacing channel includes ring electrode 33a and tip electrode 33b of bipolar lead 33c, sense amplifier 31, pulse generator 32, and a channel interface 30. The channel interfaces communicate bi-directionally with a port of microprocessor 10 and may include analog-to-digital converters for digitizing sensing signal inputs from the sensing amplifiers, registers that can be written to for adjusting the gain and threshold values of the sensing amplifiers, and registers for controlling the output of pacing pulses and/or changing the pacing pulse amplitude. A shock pulse generator 20 is also interfaced to the controller for delivering defibrillation shocks through electrodes selected by the switch matrix. In the illustrated embodiment, the device is equipped with bipolar leads that include two electrodes which are used for outputting a pacing pulse and/or sensing intrinsic activity. Other embodiments may employ unipolar leads with single electrodes for sensing and pacing. The switch matrix 70 may configure a channel for unipolar sensing or pacing by referencing an electrode of a unipolar or bipolar lead with the device housing or can 60.

The controller 10 controls the overall operation of the device in accordance with programmed instructions stored in memory. The controller 10 interprets electrogram signals from the sensing channels in order to control the delivery of paces in accordance with a pacing mode and/or deliver shock therapy in response to detection of a tachyarrhythmia such as ventricular fibrillation. The sensing circuitry of the device generates atrial and ventricular electrogram signals from the voltages sensed by the electrodes of a particular channel. An electrogram is analogous to a surface ECG and indicates the time course and amplitude of cardiac depolarization that occurs during either an intrinsic or paced beat. When an electrogram signal in an atrial or sensing channel exceeds a specified threshold, the controller detects an atrial or ventricular sense, respectively, which may also be referred to as a P-wave or R-wave in accordance with its representation in a surface ECG. The controller may use sense signals in pacing algorithms in order to trigger or inhibit pacing and to derive heart rates by measuring the time intervals between senses.

As described above, sensing channels include sense amplifier circuits for amplifying and filtering electrogram signals picked up by electrodes placed in or on the heart and which are coupled by suitable leads to the implantable cardiac rhythm management device. In some devices, the signals emanating from the sense amplifier (the sensing signals) are applied to one input of a comparator circuit whose other input is connected to a source of reference potential. Only when an electrogram signal from the sense amplifier exceeds the reference potential threshold will it be treated as a detected cardiac depolarization event such that an atrial or ventricular sense is detected. The source reference potential may thus be referred to as a sensing threshold. Other devices implement the comparator function in software such that a digitized electrogram signal value is compared with a reference value in order to detect the depolarization event. In such devices, the sensing signals would typically be digitized through an Analog-to-Digital Converter (ADC) residing in the Channel Interface 30 or 40. Implementing the sensing threshold digitally also allows it to more easily be made a dynamic threshold which varies in time, typically (though not necessarily) updated on a beat by beat basis. Such a time-varying sensing threshold, sometimes referred to as a threshold profile or template, is implemented so that it starts at a value related additively or proportionally to the peak absolute amplitude of a detected cardiac depolarization and then generally falls or decays over time following some predetermined shape. As such, the sensing system becomes more sensitive as more time passes from the previously detected cardiac depolarization. Eventually, such a decaying threshold value will reach a minimum value, sometimes called a sensing floor, if no other cardiac depolarizations are detected first. The sensing floor may be set at a predetermined constant value, or it could be related additively or proportionally to the starting value.

2. Estimation of Noise Level and Noise Floor

When noise levels in the electrocardiogram approach the sensing threshold, the likelihood of oversensing increases (i.e., false detection of depolarization events). If the sensing threshold is increased too high in an attempt to overcome the effects of noise, on the other hand, the likelihood of undersensing (i.e., failing to detect true depolarization events) is increased. It would therefore be desirable to adjust the value of a sensing threshold in accordance with the magnitude of any noise which may be present. The present invention provides a means for estimating the magnitude of noise when such noise is determined to present, referred to as the estimated noise level. When noise is determined not to be present, the ambient noise level may also be is estimated, referred to as the estimated noise floor. Both the estimated noise level and the estimated noise floor may then be used to adjust the sensitivity of a sensing channel at times when noise is determined to be present or absent, respectively, in that channel.

The following is a description of an exemplary embodiment of the method for detecting the presence of noise in a sensing channel which may be implemented by appropriate programming of the controller of a device. The algorithm may be executed for any or all of the device's sensing channels. The device samples an electrogram signal from one of its sensing channels to obtain a series of samples, where each sample can be designated by $X[n]$ with $n$ an integer. It is then determined whether each sample represents a local peak or not, where the term local peak refers to an extremum in the electrogram signal. A sample $X[n]$ is a local peak if its amplitude is either: 1) greater than the amplitude of the preceding sample $X[n-1]$ by at least a specified threshold value $\delta_1$ and also greater than the amplitude of the subsequent sample $X[n+1]$ by at least the specified threshold $\delta_2$, or 2) less than the amplitude of the preceding sample X[n−1] by at least a specified threshold $\delta_3$ and also less than the amplitude of the subsequent sample X[n+1] by at least the specified threshold $\delta_4$. The simplest embodiment would have $\delta_1=\delta_2=\delta_3=\delta_4=\delta$. For a digital implementation, $\delta$ could be fixed to a predetermined number of LSB codes of the A/D converter.

The device then computes a local peak density, where the local peak density refers to a measure of how frequently local peaks are occurring in the sampled electrogram signal. For example, the local peak density may be computed by counting the number of local peaks in a predetermined number of samples. A noise flag is then computed to be either set or cleared in accordance with the computed local peak density, where the noise flag is set if the local peak density exceeds a first threshold value. (As used herein, the terms "setting" and "clearing" should be taken to mean changing the noise flag to whatever value is used to indicate that noise is present or absent, respectively, and not necessarily or exclusively to the setting and clearing of a bit.) When the noise flag is set, a noise level in the electrogram signal may be estimated by computing a noise statistic from a series of samples X[n] collected over the range of values of n associated with the time at which the noise flag is set, where the range of values of n may begin and end entirely before or after the noise flag is set, or may surround the time at which the noise flag is set. The values of n over this range need not be contiguous, but should be chosen to represent a local period where the noise level to be measured is substantially stationary.

The noise flag is cleared when the local peak density in the predetermined number of consecutive samples falls below a second threshold value, where the second threshold value may be the same as or less than the first threshold value. In the latter case, the algorithm exhibits hysteretic behavior in setting and clearing of the noise flag. When the noise flag is cleared, a noise floor in the electrogram signal may be estimated by calculating a noise statistic from a series of samples X[n] collected over the range of values of n associated with the time at which the noise flag is cleared, where the noise statistic used to estimate the noise floor may be the same or different from the noise statistic used to estimate the noise level. The range of values of n used for estimating the noise floor may begin and end entirely before or after the noise flag is cleared, or may surround the time at which the noise flag is cleared. The values of n over this range need not be contiguous, but should be chosen to represent a local period where the noise floor to be measured is substantially stationary, and should consist of periods in between cardiac cycles where the sensed signal is substantially quiescent.

Examples of noise statistics which may be used to estimate the noise level or noise floor include an absolute peak, a mean of absolute values, a median of absolute values, a mode of absolute values (such as a most likely absolute value which may be found as the peak of a probability density estimate), a root-mean square, and a mean square over the series of collected electrogram samples. The noise statistic may also be computed as a moving average, an autoregressive average, or a cascade or linear combination of such previously computed noise statistics or averages of such previously computed noise statistics.

Figure 2:
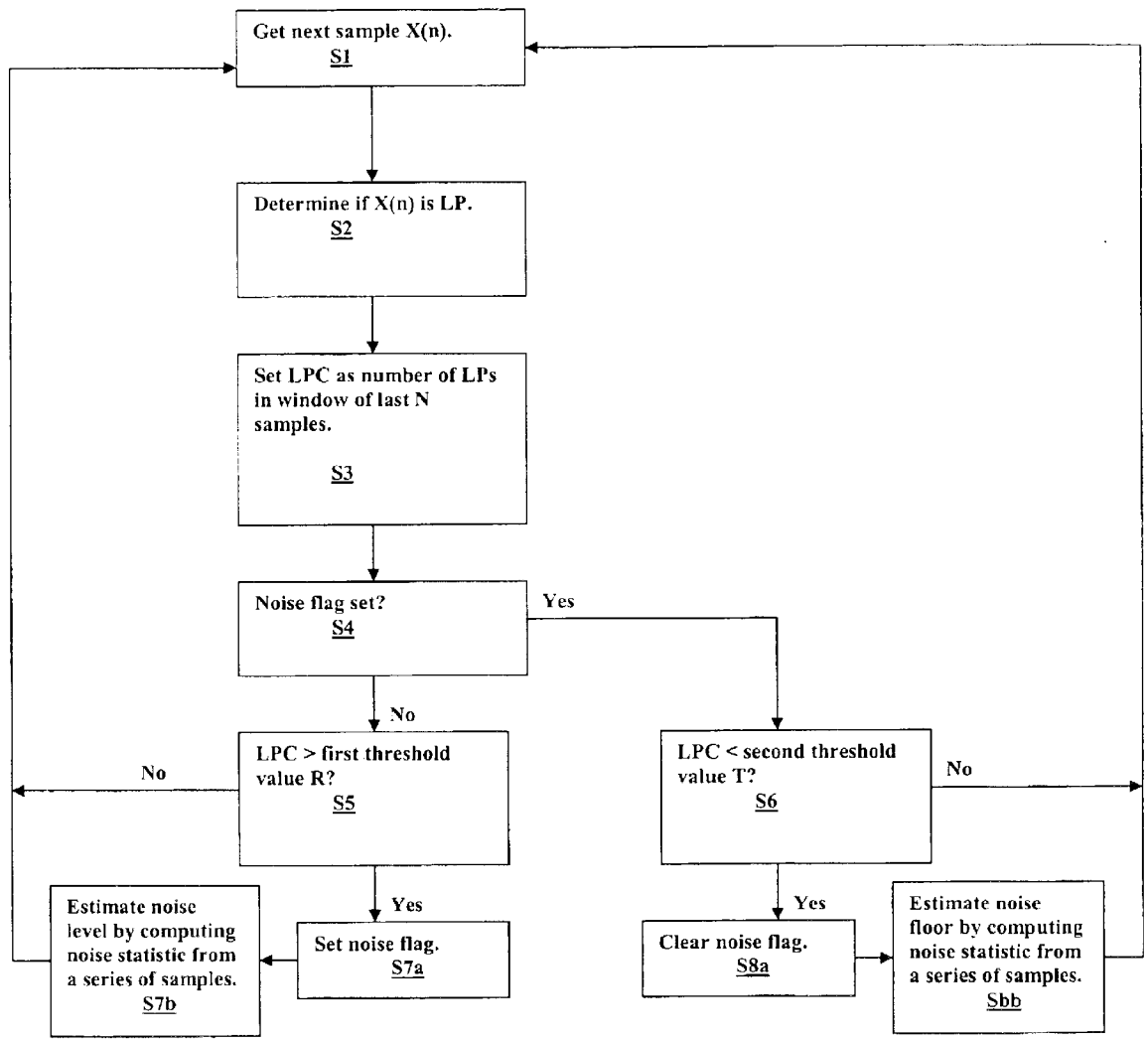
FIG. 2 illustrates an exemplary algorithm for detecting the presence of noise in a sensing channel.

FIG. 2 illustrates the steps involved in an exemplary implementation of an algorithm for detecting when noise is present or absent which exhibits hysteresis. At step S1, the next electrogram sample X(n) in the sequence of samples is obtained. At step S2, it is determined whether or not the sample X(n) is a local peak LP. At step S3, a local peak density in a predetermined number of samples is calculated as a local peak count LPC which is the number of local peaks counted in a moving window of the last N samples. At step S4, the device checks whether the noise flag is set or not. If the noise flag is cleared, the local peak count LPC is compared with a first specified threshold value R at step S5. If the local peak count LPC does not exceed R, the device returns to step S1 to get the next sample. If the local peak count LPC is greater than R, then the noise flag is set at step S7a and the noise level is estimated by computing a noise statistic from a series of samples at step S7b before returning to step S1. If at step S4, it is determined that the noise flag is set, the device compares the local peak count LPC with a second specified threshold value T at step S6, where the threshold value T is less than the threshold value R. If the local peak count LPC is not less than T, the device returns to step S1 to get the next sample. If the local peak count LPC is less than T, then the noise flag is cleared at step S8a and the noise floor is estimated by computing a noise statistic from a series of samples at step S8b before returning to step S1.

In another embodiment of the method, use is made of the fact that an electrogram which contains a depolarization complex, such as a QRS complex in the case of a ventricular depolarization, will contain relatively few local peaks. Thus, the method may further include the step of detecting a QRS complex when a beat statistic computed from a predetermined number of consecutive samples exceeds a specified beat threshold value and excluding a range of samples around the sample where QRS complex is detected from the computation of the noise statistic used to estimate the noise level. The beat statistic may be, for example, a weighted average of the absolute values of the predetermined number of consecutive samples. Beat detection may also be used to exclude sample values from computation of the noise flag, where the method then includes the step of detecting a QRS complex when a beat statistic computed from a predetermined number of consecutive samples exceeds a specified beat threshold value and excluding a range of samples around the sample where QRS complex is detected from the computation of the local peak density used to compute the noise flag.

In another variation of the method, rather than employing a single moving window containing a predetermined number of electrogram samples for computation of the noise flag, a plurality of windows may be used where local peaks are counted in each window. In this embodiment, the number of local peaks in each of a predetermined number of consecutive windows of consecutive samples are counted, and each such window is declared as noisy if the number of local peaks in that window exceeds a specified threshold value K. The windows may overlap one another in time, they may be located end to end, or they may be disjoint in time, as needed to substantially represent the local peak behavior of the sensing signal at each time window. The noise flag is then set if the number of noisy windows in the predetermined number of windows exceeds a first threshold value and is cleared if the number of noisy windows is less than a second threshold value, where hysteresis is exhibited if the second threshold value is less than the first threshold value. Alternatively, a local peak score may be computed for each of a predetermined number of consecutive windows of consecutive samples, where the local peak score of each window is the number of local peaks in that window, and a local peak score statistic is then computed for the predetermined number of consecutive windows. Examples of a local peak score statistic include a sum, a maximum value, a mean, a median, a mode, a mean square, and a root-mean square of the local peak scores of the predetermined number of windows. The noise flag is then set if the local peak score statistic exceeds a first threshold value and is cleared if the local peak score statistic is below a second threshold value. Similar to the earlier described embodiment, the noise statistic used to estimate the noise level or noise floor may be computed from the samples in the predetermined number of consecutive windows or from subsequent samples after the noise flag is either set or cleared. Beat detection may also be employed in this embodiment, where the method then includes the steps of detecting a QRS complex when a beat statistic computed from a predetermined number of consecutive samples exceeds a specified beat threshold value and excluding windows containing a detected QRS complex from the computation of the noise statistic used to estimate the noise level or noise floor.

As noted, estimation of the noise level and noise floor may be used by the device to adjust the sensitivity of a sensing channel. For example, the device may be programmed to adjust the sensing threshold or threshold profile of a sensing amplifier in a particular sensing channel in accordance with the estimated noise level when the noise flag is set and in accordance with the estimated noise floor when the noise flag is cleared. Such adjustment of the sensing threshold may be performed, for example, by multiplying a nominal threshold value by a proportionality constant based upon the estimated noise level or noise floor, and/or by adding a constant value to the sensing threshold, where the constant value is based upon the estimated noise level or noise floor. For a threshold profile, similar multiplicative or additive adjustments may be performed on the nominal starting value, the nominal decay rate, the nominal sensing floor, or combinations of these values, to adjust the profile based upon the estimated noise level or noise floor. One embodiment of such adjustments could include setting these parameters to ensure the sensing floor always exceeds, by a predetermined margin, the noise level when the noise flag is set, or the noise floor when the noise flag is cleared.

The estimated noise level and noise floor may also be used by the device to alter its operation in other ways. For example, the device may discontinue use of a particular sensing channel if the estimated noise level or noise floor exceeds a specified limit value. When alternative sensing channels are available, the device may also select for use that sensing channel in which the noise level or noise floor estimate is lowest.

Although the invention has been described in conjunction with the foregoing specific embodiments, many alternatives, variations, and modifications will be apparent to those of ordinary skill in the art. Other such alternatives, variations, and modifications are intended to fall within the scope of the following appended claims.

What is claimed is:

1. A method for operating a cardiac rhythm management device, comprising:
   sampling an electrogram signal from a sensing channel of the device to obtain a series of samples, where each sample can be designated by X[n] with n an integer;
   determining whether each sample represents a local peak or not, wherein a sample X[n] is a local peak if its amplitude is either: 1) greater than the amplitude of the preceding sample X[n−1] by a specified threshold value $\delta_1$ and also greater than the amplitude of the subsequent sample X[n+1] by the specified threshold $\delta_2$, or 2) less than the amplitude of the preceding sample X[n−1] by a specified threshold $\delta_3$ and also less than the amplitude of the subsequent sample X[n+1] by the specified threshold $\delta_4$;
   computing a local peak density in a predetermined number of consecutive samples;
   computing a noise flag as either set or cleared in accordance with the computed local peak density, wherein the noise flag is set if the local peak density exceeds a first threshold value; and,
   estimating a noise level in the electrogram signal by computing a noise statistic from a series of samples when the noise flag is set.

2. The method of claim 1 further comprising clearing the noise flag when the local peak density in the predetermined number of consecutive samples falls below a second threshold value, wherein the second threshold value is less than the first threshold value.

3. The method of claim 2 further comprising estimating a noise floor in the electrogram signal by calculating a noise statistic from a series of samples when the noise flag is cleared.

4. The method of claim 3 wherein the noise level or noise floor is estimated on a beat-to-beat basis.

5. The method of claim 3 wherein the noise level or noise floor is estimated each time the noise flag is set or cleared, respectively.

6. The method of claim 3 wherein the noise level or noise floor is estimated at predetermined time intervals.

7. The method of claim 3 further comprising detecting a QRS complex when a beat statistic computed from a predetermined number of consecutive samples exceeds a specified beat threshold value and excluding a range of samples around the sample where QRS complex is detected from the computation of the noise statistic used to estimate the noise level or the noise floor.

8. The method of claim 7 wherein the beat statistic is a weighted average of the predetermined number of consecutive samples.

9. The method of claim 3 further comprising adjusting a sensing threshold or threshold profile of a sensing amplifier in accordance with the estimated noise floor when the noise flag is cleared.

10. The method of claim 9 wherein the sensing threshold, a starting value, decay rate, or sensing floor of the threshold profile, is adjusted by multiplying its nominal value by a coefficient and then adding an offset value to the result, where the offset value and coefficient value are based upon the estimated noise floor.

11. The method of claim 1 wherein the calculated noise statistic is selected from a group consisting of an absolute peak, a mean of absolute values, a median of absolute values, a mode of absolute values, a root-mean square, and a mean square over the series of collected electrogram samples.

12. The method of claim 1 wherein the noise statistic is calculated from the same samples in which the local peak density is computed to set or clear the noise flag.

13. The method of claim 1 wherein the noise statistic is calculated from a predetermined series of samples associated with the time when the noise flag is set or cleared.

14. The method of claim 1 wherein the local peak density is computed by counting the number of local peaks in the predetermined number of samples.

15. The method of claim 1 further comprising detecting a QRS complex when a beat statistic computed from a predetermined number of consecutive samples exceeds a specified beat threshold value and excluding a range of samples around the sample where QRS complex is detected from the computation of the local peak density used to compute the noise flag.

16. The method of claim 1 further comprising:
  counting the number of local peaks in a predetermined number of consecutive windows each of consecutive samples;
  declaring a window as noisy if the number of local peaks in the window exceeds a specified threshold value K;
  setting the noise flag if the number of noisy windows in the predetermined number of windows exceeds the first threshold value.

17. The method of claim 16 further comprising computing the noise statistic used to estimate the noise level from the samples in the predetermined number of consecutive windows.

18. The method of claim 16 further comprising detecting a QRS complex when a beat statistic computed from a predetermined number of consecutive samples exceeds a specified beat threshold value and excluding windows containing a detected QRS complex from the computation of the noise statistic used to estimate the noise level.

19. The method of claim 1 further comprising:
  computing a local peak score for each of a predetermined number of consecutive windows each of consecutive samples, where the local peak score of each window is the number of local peaks in that window;
  computing a local peak score statistic for the predetermined number of consecutive windows; and,
  setting the noise flag if the local peak score statistic exceeds the first threshold value.

20. The method of claim 19 wherein the local peak score statistic is selected from a group consisting of a sum, a maximum value, a mean, a median, a mode, a mean square, and a root-mean square of the local peak scores of the predetermined number of windows.

21. The method of claim 1 wherein the noise statistic is computed as a moving average, an autoregressive average, or a cascade or linear combination of previously computed noise statistics or averages of previously computed noise statistics.

22. The method of claim 1 further comprising adjusting a sensing threshold or threshold profile of a sensing amplifier in accordance with the estimated noise level when the noise flag is set.

23. The method of claim 22 wherein the sensing threshold, a starting value, decay rate, or sensing floor of the threshold profile, is adjusted by multiplying its nominal value by a coefficient and then adding an offset value to the result, where the offset value and coefficient value are based upon the estimated noise level.

24. A cardiac rhythm management device, comprising:
  one or more sensing channels for sensing intrinsic cardiac activity;
  means for sampling an electrogram signal from a sensing channel of the device to obtain a series of samples, where each sample can be designated by X[n] with n an integer;
  means for determining whether each sample represents a local peak or not, wherein a sample X[n] is a local peak if its amplitude is either: 1) greater than the amplitude of the preceding sample X[n−1] by a specified threshold value $\delta_1$ and also greater than the amplitude of the subsequent sample X[n+1] by the specified threshold $\delta_2$, or 2) less than the amplitude of the preceding sample X[n−1] by a specified threshold $\delta_3$ and also less than the amplitude of the subsequent sample X[n+1] by the specified threshold $\delta_4$;
  means for computing a local peak density in a predetermined number of consecutive samples;
  means for computing a noise flag as either set or cleared in accordance with the computed local peak density, wherein the noise flag is set if the local peak density exceeds a first threshold value; and,
  means for estimating a noise level in the electrogram signal by computing a noise statistic from the series of samples when the noise flag is set.

25. The device of claim 24 further comprising adjusting a sensing threshold of a sensing channel in accordance with the estimated noise level when the noise flag is set.

* * * * *

UNITED STATES PATENT AND TRADEMARK OFFICE
CERTIFICATE OF CORRECTION

PATENT NO. : 6,917,830 B2
DATED : July 12, 2005
INVENTOR(S) : Palreddy et al.

It is certified that error appears in the above-identified patent and that said Letters Patent is hereby corrected as shown below:

Title page,
Item [75], Inventors, delete "Vadnais Heights, MN" and insert -- Mission Viejo, CA --.

Signed and Sealed this

Tenth Day of January, 2006

JON W. DUDAS
*Director of the United States Patent and Trademark Office*